(12) United States Patent
Jingu (10) Patent No.: US 11,493,472 B2
(45) Date of Patent: Nov. 8, 2022

(54) SENSOR DEVICE AND MEASUREMENT APPARATUS

(71) Applicant: SONY SEMICONDUCTOR SOLUTIONS CORPORATION, Kanagawa (JP)

(72) Inventor: Motoko Jingu, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 50 days.

(21) Appl. No.: 16/753,387

(22) PCT Filed: Sep. 20, 2018

(86) PCT No.: PCT/JP2018/034843
§ 371 (c)(1),
(2) Date: Apr. 3, 2020

(87) PCT Pub. No.: WO2019/073774
PCT Pub. Date: Apr. 18, 2019

(65) Prior Publication Data
US 2020/0333280 A1 Oct. 22, 2020

(30) Foreign Application Priority Data
Oct. 11, 2017 (JP) .............................. JP2017-197537

(51) Int. Cl.
*G01N 27/327* (2006.01)
*G01N 27/30* (2006.01)
(Continued)

(52) U.S. Cl.
CPC ............. *G01N 27/301* (2013.01); *G01K 7/01* (2013.01); *G01N 27/4065* (2013.01); *G01N 33/4836* (2013.01); *G01N 33/48728* (2013.01)

(58) Field of Classification Search
CPC .............. G01N 33/4836; G01N 33/48728
See application file for complete search history.

(56) References Cited

U.S. PATENT DOCUMENTS 6,132,683 A * 10/2000 Sugihara ............ G01N 33/4836
204/403.01
6,277,629 B1 * 8/2001 Wolf ..................... B01L 3/5027
257/414
(Continued)

FOREIGN PATENT DOCUMENTS

JP 2004-333485 11/2004
JP 2009-529909 8/2009
(Continued)

OTHER PUBLICATIONS

Wang et al., "Neural Probes with Integrated Temperature Sensors for Monitoring Retina and Brain Implantation and Stimulation," IEEE Transactions on Neural Systems and Rehabilitation Engineering, vol. 25, No. 9, Sep. 2017, pp. 1663-1673 (Year: 2017).*
(Continued)

*Primary Examiner* — Alexander S Noguerola
(74) *Attorney, Agent, or Firm* — Sheridan Ross P.C.

(57) ABSTRACT

To provide a sensor device and a measurement apparatus that are able to appropriately control a temperature of a sensing region where a potential is measured. Provided is a sensor device that includes an electrode array exposed to a sensing region, at least one or more wiring line layers provided in a layer same as the electrode array, a temperature determiner that determines a temperature of the sensing region on the basis of an electric resistance of the wiring line layer, and a temperature controller that controls the temperature of the sensing region on the basis of the temperature of the sensing region determined by the temperature determiner.

20 Claims, 5 Drawing Sheets

(51) Int. Cl.
    *G01K 7/01*    (2006.01)
    *G01N 27/406*    (2006.01)
    *G01N 33/487*    (2006.01)
    *G01N 33/483*    (2006.01)

(56) References Cited

U.S. PATENT DOCUMENTS

| | | | |
|---|---|---|---|
| 6,730,199 B1 * | 5/2004 | Hanni | C12M 41/46 204/403.02 |
| 2004/0214312 A1 | 10/2004 | Tyvoll et al. | |
| 2005/0279634 A1 | 12/2005 | Ozaki et al. | |
| 2010/0156444 A1 | 6/2010 | Ponjee et al. | |
| 2013/0230881 A1 | 9/2013 | Yasuda et al. | |
| 2018/0267005 A1 | 9/2018 | Ando et al. | |

FOREIGN PATENT DOCUMENTS

| | | |
|---|---|---|
| JP | 2009-287934 | 12/2009 |
| JP | 2015-059929 | 3/2015 |
| JP | 2016-041074 | 3/2016 |
| WO | WO 2005/001018 | 1/2005 |
| WO | WO 2017/122338 | 7/2017 |

OTHER PUBLICATIONS

EPO computer-generated English language translation of JP 2015-59929 A, downloaded Oct. 23, 2021 (Year: 2015).*
International Search Report and Written Opinion prepared by the Japanese Patent Office dated Dec. 12, 2018, for International Application No. PCT/JP2018/034843.

* cited by examiner

SENSOR DEVICE AND MEASUREMENT APPARATUS

CROSS REFERENCE TO RELATED APPLICATIONS

This application is a national stage application under 35 U.S.C. 371 and claims the benefit of PCT Application No. PCT/JP2018/034843 having an international filing date of 20 Sep. 2018, which designated the United States, which PCT application claimed the benefit of Japanese Patent Application No. 2017-197537 filed 11 Oct. 2017, the entire disclosures of each of which are incorporated herein by reference.

TECHNICAL FIELD

The present disclosure relates to a sensor device and a measurement apparatus.

BACKGROUND ART

A potential measurement device has been known in which minute electrodes are arranged in an array and which electrochemically measures a potential generated in a region on the electrodes. For example, by filling the region on the electrodes arranged in an array with culture solution, such a sensor potential measurement device is used to measure an action potential generated by a living cell cultured in the culture solution.

PTL 1 below discloses a potential measurement device that is able to measure potentials at multiple points at the same time by integrating an electrode, an amplifier, an A/D (Analog/Digital) converter, and the like on a single substrate by using CMOS (Complementary Metal-Oxide-Semiconductor) integrated circuit technology.

CITATION LIST

Patent Literature

PTL 1: WO 2017/061171

SUMMARY OF THE INVENTION

Problems to be Solved by the Invention

However, according to the potential measurement device disclosed in PTL 1 described above, a temperature of the region where the potential is measured fluctuates as the measurement progresses. One reason for this is that a great amount of heat is generated as the measurement progresses since a large number of elements that may generate heat, such as the electrode, the amplifier, the A/D converter, or the like are integrated on the single substrate in the potential measurement device disclosed in PTL 1.

Here, a reaction speed of a reaction of solution on the electrodes may fluctuate depending on a temperature. Furthermore, in a case where the potential measurement device measures an action potential of a living cell, a frequency of an activity of the living cell largely varies depending on the temperature.

Therefore, it has been requested for the sensor device in which the minute electrodes are arranged in an array and which electrochemically measures the potential on the electrodes to easily detect a temperature of a sensing region where the potential is measured and appropriately control the temperature of the sensing region.

Means for Solving the Problems

According to the present disclosure, a sensor device is provided that includes an electrode array exposed to a sensing region, at least one or more wiring line layers provided in a layer same as the electrode array, a temperature determiner that determines a temperature of the sensing region on the basis of an electric resistance of the wiring line layer, and a temperature controller that controls the temperature of the sensing region on the basis of the temperature of the sensing region determined by the temperature determiner.

Furthermore, according to the present disclosure, a measurement apparatus is provided that includes a sensor device and an information processing device that executes information processing on an output from the sensor device, in which the sensor device includes an electrode array exposed to a sensing region, at least one or more wiring line layers provided in a layer same as the electrode array, a temperature determiner that determines a temperature of the sensing region on the basis of an electric resistance of the wiring line layer, and a temperature controller that controls the temperature of the sensing region on the basis of the temperature of the sensing region determined by the temperature determiner.

According to the present disclosure, it is possible to determine the temperature of the sensing region from the electric resistance of the wiring line layer provided in the layer same as the electrode array and to appropriately heat or cool the sensing region by the temperature controller on the basis of the determined temperature.

Effects of the Invention

As described above, according to the present disclosure, it is possible to appropriately control a temperature of a sensing region where a potential is measured.

Note that the above effects are not necessarily limited, and any effect described herein or another effect that may be recognized from the present specification may be obtained together with or instead of the above effects.

MODES FOR CARRYING OUT THE INVENTION

Preferred embodiments of the present disclosure will be described in detail below with reference to the attached drawings. Note that components having a substantially same functional configuration are denoted with the same reference numeral in the specification and the drawings, and accordingly, overlapped description will be omitted.

Note that the description will be made in the following order.
1. Sensor Device
  1.1. Configuration of Sensor Device
  1.2. Control of Sensor Device
  1.3. Variation of Planar Arrangement of Wiring Line Layer
  1.4. Modification Example of Sensor Device
  1.5. Summary of Sensor Device
2. Measurement Apparatus <1. Sensor Device>
(1.1. Configuration of Sensor Device)

Figure 1:
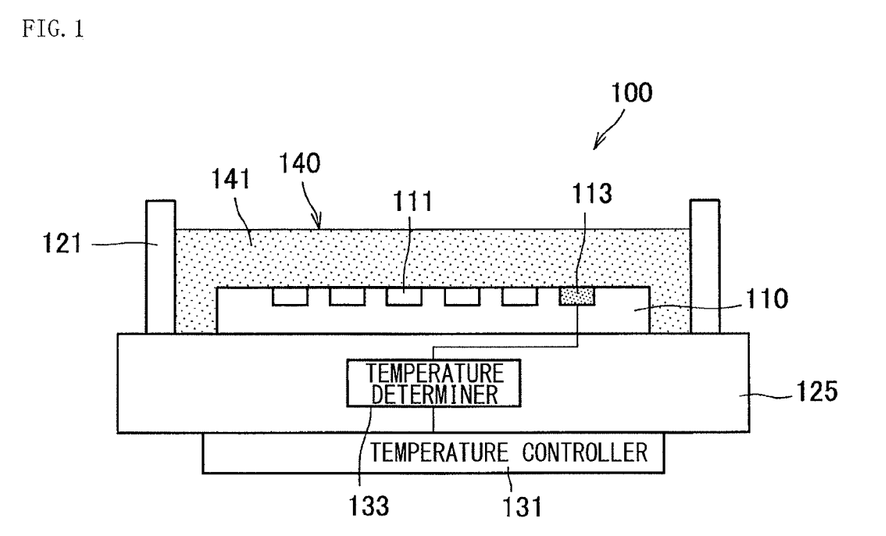
FIG. 1 is a cross-sectional diagram schematically illustrating a configuration of a sensor device according to a first embodiment of the present disclosure.
Figure 2:
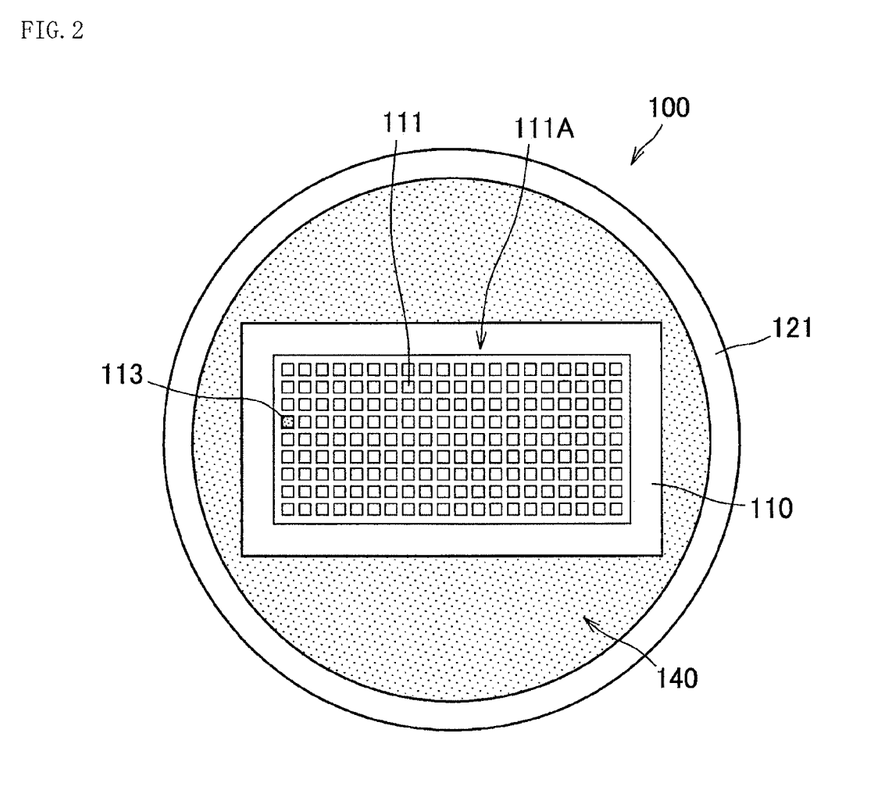
FIG. 2 is a top view schematically illustrating the configuration of the sensor device according to the first embodiment.

First, a configuration of a sensor device according to a first embodiment of the present disclosure will be described with reference to FIGS. 1 and 2. FIG. 1 is a cross-sectional diagram schematically illustrating the configuration of the sensor device according to the present embodiment. FIG. 2 is a top view schematically illustrating the configuration of the sensor device according to the present embodiment.

As illustrated in FIG. 1, a sensor device 100 includes an electrode array 111, a wiring line layer 113, a semiconductor substrate 110, a structural member 125, a sidewall 121, a temperature determiner 133, and a temperature controller 131. The sensor device 100 is a potential measurement device which measures a potential at each position of a sensing region 140 in a recess structure formed by the structural member 125 and the sidewall 121. Note that, for example, solution 141 such as culture solution is introduced into the sensing region 140.

The electrode array 111 includes a plurality of detection electrodes and a reference electrode arranged in an array and is provided by arranging the detection electrodes and the reference electrode on one main surface of the semiconductor substrate 110 exposed to the sensing region 140.

Each of the plurality of detection electrodes detects a potential generated by a measurement target at each position of the sensing region 140. The detection electrodes are vertically and horizontally arranged at periodic intervals (aligned in a so-called matrix), for example, in a plane region within the sensing region 140 on which the measurement target may be arranged. Note that the plane region where the detection electrodes are arranged is also referred to as an array region. The reference electrode acquires a reference potential to be a reference used to detect a change in the potential detected by the detection electrode. The reference electrode is arranged at a position away from the array region, for example, not to receive an effect of the potential generated by the measurement target. This enables the reference electrode to acquire a reference potential that does not fluctuate with respect to the potential detected by the detection electrode and that may be a reference.

However, the above-described planar arrangement of the detection electrodes and the reference electrode is a merely an example. It goes without saying that the detection electrodes and the reference electrode may be provided on one main surface of the semiconductor substrate 110 in any alignment.

The measurement target of the sensor device 100 is, for example, a living cell, and more specifically, a cardiomyocyte, a nerve cell, or the like that generates an action potential. These living cells perform ion uptake and release by a cellular activity. Therefore, it is possible for the sensor device 100 to measure the action potential of the living cell which is the measurement target by reading an ion change amount by the detection electrode via the solution 141 that fills the sensing region 140. Specifically, it is possible for the sensor device 100 to read the action potential of the living cell and the like by converting the change in the ion amount that is locally generated in the living cell into a charge amount of the detection electrode (that is, a potential difference from the reference electrode) via the solution 141 that is a resistance.

The wiring line layer 113 is provided in the same layer as the electrode array 111 in the semiconductor substrate 110. The wiring line layer 113 may be exposed to the sensing region 140 similarly to the electrode array 111, or it is not necessary for the wiring line layer 113 to be exposed to the sensing region 140. The wiring line layer 113 includes an electrically conductive material and is energized constantly or at a predetermined timing. Since an electric resistance of a substance varies depending on temperature, it is possible for the sensor device 100 to determine the temperatures of the wiring line layer 113 and the sensing region 140 close to the wiring line layer 113 by detecting the electric resistance of the wiring line layer 113. This enables the sensor device 100 to determine the temperature of the sensing region 140 with a simple structure. Therefore, it is possible for the sensor device 100 to stabilize the temperature of the sensing region 140 by performing temperature control to cause the temperature of the sensing region 140 to fall within a predetermined range.

The wiring line layer 113 may include an electrically conductive material of which the electric resistance largely varies depending on temperature. For example, the wiring line layer 113 may include a metal material of which the electric resistance relatively and linearly varies depending on temperature. This enables the sensor device 100 to determine the temperatures of the wiring line layer 113 and the sensing region 140 with higher accuracy on the basis of the electric resistance of the wiring line layer 113.

More specifically, the wiring line layer 113 may include noble metal. The wiring line layer 113 may include noble metal, such as gold (Au), silver (Ag), platinum (Pt), palladium (Pd), rhodium (Rh), iridium (Zr), ruthenium (Ru), or osmium (Os), or an alloy of these noble metals. The noble metal, ionization tendency of which is smaller than that of hydrogen, is slightly soluble in the solution 141. Therefore, by forming the wiring line layer 113 by using the above noble metal, it is possible for the sensor device 100 to reduce harmfulness applied from the wiring line layer 113 to the living cell and the like that is the measurement target.

For example, the wiring line layer 113 may include the same material as that of the electrode array 111. Since the wiring line layer 113 is provided in the same layer as the electrode array 111 in the semiconductor substrate 110, in a case where the wiring line layer 113 and the electrode array 111 include the same materials, it is possible to concurrently form the wiring line layer 113 and the electrode array 111 in a manufacturing process of the sensor device 100. This makes it possible to further simplify the manufacturing process of the sensor device 100.

Here, the planar arrangement of the electrode array 111 and the wiring line layer 113 will be described with reference to FIG. 2.

As illustrated in FIG. 2, the electrode array 111 is provided, for example, by vertically and horizontally aligning the plurality of minute detection electrodes in a matrix with periodic intervals on the semiconductor substrate 110. That is, a plane region where the electrode array 111 is arranged is a region where it is possible to measure the potential (also referred to as an array region 111A). Note that some electrodes provided in a peripheral portion of the array region 111A may function as the reference electrodes used to acquire the reference potentials.

For example, at least one or more wiring line layers 113 are provided in the peripheral portion of the array region 111A. Since the wiring line layer 113 is provided in the array region 111A, it is possible for the sensor device 100 to accurately determine a temperature of a region within the sensing region 140 where the measurement target exists. Since it is sufficient that the wiring line layer 113 be able to detect the electric resistance that fluctuates depending on temperature by energization, an area and a planar shape of the wiring line layer 113 may be respectively any area and any planar shape. However, the wiring line layer 113 may have the same planar shape as that of one of the minute detection electrodes of the electrode array 111. This enables the wiring line layer 113 to be formed under the same manufacturing condition as that of the electrode array 111, simplifying the manufacturing process.

The semiconductor substrate 110 is a substrate having one main surface on which the electrode array 111 and the wiring line layer 113 are provided and includes a semiconductor material. Since it is possible to process the semiconductor substrate 110 through a microfabrication process that is used to manufacture a semiconductor apparatus such as a CMOS image sensor, it is possible to easily miniaturize the electrode array 111 and the wiring line layer 113. Furthermore, a signal processing circuit that transfers, amplifies, and A/D converts the potential detected by the electrode array 111 is further provided on the semiconductor substrate 110. As described above, it is possible to easily form these signal processing circuits (circuits including a transistor and the like) on the semiconductor substrate 110 by applying the microfabrication process used to manufacture a semiconductor apparatus, such as the CMOS image sensor.

The semiconductor substrate 110 may be a substrate including, for example, a semiconductor material such as silicon. However, it goes without saying that the semiconductor substrate 110 may be a substrate including other semiconductor material, such as a germanium (Ge) substrate, a gallium arsenide (GaAs) substrate, a gallium nitride (GaN) substrate, or a silicon carbide (SiC) substrate.

The structural member 125 is a structure component of the sensor device 100 and holds the semiconductor substrate 110. Furthermore, the structural member 125 includes the temperature determiner 133 and includes the temperature controller 131 on a surface opposed to the surface of the structural member 125 holding the semiconductor substrate 110. The structural member 125 forms a recess structure together with the sidewall 121 to define the sensing region 140 in the recess structure. The structural member 125 may include various glass or various resins having a certain degree of strength. For example, the structural member 125 may include various resins such as a polyethylene resin, a polypropylene resin, a polyester resin, a fluoroethylene resin such as Teflon (registered trademark), a polycarbonate resin, or an ABS (acrylonitrile butadiene styrene) resin.

The sidewall 121 is projected from the one main surface of the structural member 125 in a vertical direction with respect to the one main surface of the structural member 125 and is provided along the entire periphery of the structural member 125. The sidewall 121 and the structural member 125 form a recess structure in which it is possible to store the solution 141. This enables the sensor device 100 to detect a change in the potential of the measurement target placed on the sensing region 140 by using the electrode array 111 via the solution 141. Furthermore, in a case where the measurement target is a living cell, storing the culture solution as the solution 141 in the recess structure enables the sensor device 100 to measure the action potential of the living cell alive while culturing the living cell. The sidewall 121 may include, for example, various glass or various resins having a certain degree of strength similarly to the structural member 125. For example, the sidewall 121 may include various resins such as a polyethylene resin, a polypropylene resin, a polyester resin, a fluoroethylene resin such as Teflon (registered trademark), a polycarbonate resin, or an ABS resin.

The sensing region 140 is a region in the recess structure formed by the structural member 125 and the sidewall 121. The sensing region 140 is filled with the solution 141 that is electrolyte solution. A measurement target is placed on the array region 111A in the sensing region 140 and a potential is measured by the electrode array 111. For example, in a case where the measurement target is a living cell such as a nerve cell or a cardiomyocyte, the sensing region 140 is filled with culture solution of the living cell as the solution 141, and the living cell is placed on the array region 111A where the electrode array 111 is provided. This enables the sensor device 100 to measure the action potential of the living cell.

The solution 141 is electrolyte solution. Since the sensor device 100 detects the ion change amount of the solution 141 as a change in the potential by using the electrode array 111, electrolyte solution including positive ions or negative ions is used as the solution 141. It is possible to select appropriate solution 141 in accordance with the measurement target. For example, in a case where the measurement target is a living cell, the solution 141 may be the culture solution of the living cell.

The temperature determiner 133 determines the temperature of the sensing region 140 on the basis of the electric resistance of the wiring line layer 113. Specifically, first, the electric resistance of the wiring line layer 113 is detected by applying a constant current or a current at a constant voltage to the wiring line layer 113. In general, an electric resistance of a substance varies depending on temperature. Therefore, by storing a relational expression between temperature and the electric resistance of the wiring line layer 113 in advance, it is possible for the temperature determiner 133 to determine the temperature of the wiring line layer 113 on the basis of the electric resistance of the wiring line layer 113. In addition, since the wiring line layer 113 is close to or is exposed to the sensing region 140, it is possible to assume that the temperature of the wiring line layer 113 be the same as that of the sensing region 140. Therefore, it is possible for the temperature determiner 133 to determine the temperature of the wiring line layer 113 on the basis of the electric resistance of the wiring line layer 113 and to further determine the temperature of the sensing region 140. In particular, in a case where the wiring line layer 113 includes metal, the electric resistance of the wiring line layer 113 is increased in a substantially linear manner in accordance with an increase in temperature. Therefore, it is possible for the temperature determiner 133 to determine the temperature of the wiring line layer 113 by simpler calculation.

The temperature controller 131 controls the temperature of the sensing region 140. Specifically, the temperature controller 131 includes a temperature control mechanism and controls heating or cooling of the sensing region 140 by the temperature control mechanism on the basis of the temperature of the sensing region 140 determined by the temperature determiner 133. The temperature controller 131 may include, for example, both of a heating mechanism such as a heater and a cooling mechanism such as a Peltier element as the temperature control mechanisms or may include one of the heating mechanism or the cooling mechanism.

The sensor device 100 detects the change in the potential of the measurement target by an electrochemical action mechanism affected by the temperature. Therefore, in a case where the temperature of the sensing region 140 fluctuates during the measurement by the sensor device 100, there is a possibility that the measurement result fluctuates. Therefore, the temperature controller 131 may control the temperature of the sensing region 140 to maintain the temperature of the sensing region 140 to be constant. For example, the temperature controller 131 may control the temperature of the sensing region 140 to allow the temperature of the sensing region 140 to be maintained within a predetermined narrow temperature range.

Furthermore, in a case where a detection target is a living cell, the fluctuation in the temperature of the sensing region 140 largely affects a growing property and an activity of the living cell. Therefore, the temperature controller 131 may control the temperature of the sensing region 140 to fall within a temperature range appropriate for the growth of the living cell. For example, the temperature controller 131 may control the temperature of the sensing region 140 to fall within a temperature range similar to a body temperature of a host of the living cell (for example, 36° C. to 37° C. in a case of humans and mammals).

Note that the temperature controller 131 may include only the cooling mechanism such as an air-cooling fan, the Peltier element, or the like as the temperature control mechanism. This is because, in a case where the sensor device 100 includes the semiconductor substrate 110 on which the electrode array 111 including the plurality of minute electrodes and the signal processing circuit including an amplifier and an A/D converter corresponding to the electrode array 111 are integrated, a calorific value of the semiconductor substrate 110 is extremely large. In such a case it is possible for the temperature controller 131 to obtain a sufficient amount of heat from heat generated at the semiconductor substrate 110 without the necessity of preparing an additional heating mechanism for temperature control. For example, during the potential measurement by the sensor device 100, a large amount of heat is generated from the amplifier and the A/D converter that convert the potential from the electrode array 111 into a detection signal. Therefore, it is possible for the temperature controller 131 to perform temperature control to prevent the temperature of the sensing region 140 from fluctuating only by cooling with the cooling mechanism.

(1.2. Control of Sensor Device)

Figure 3:
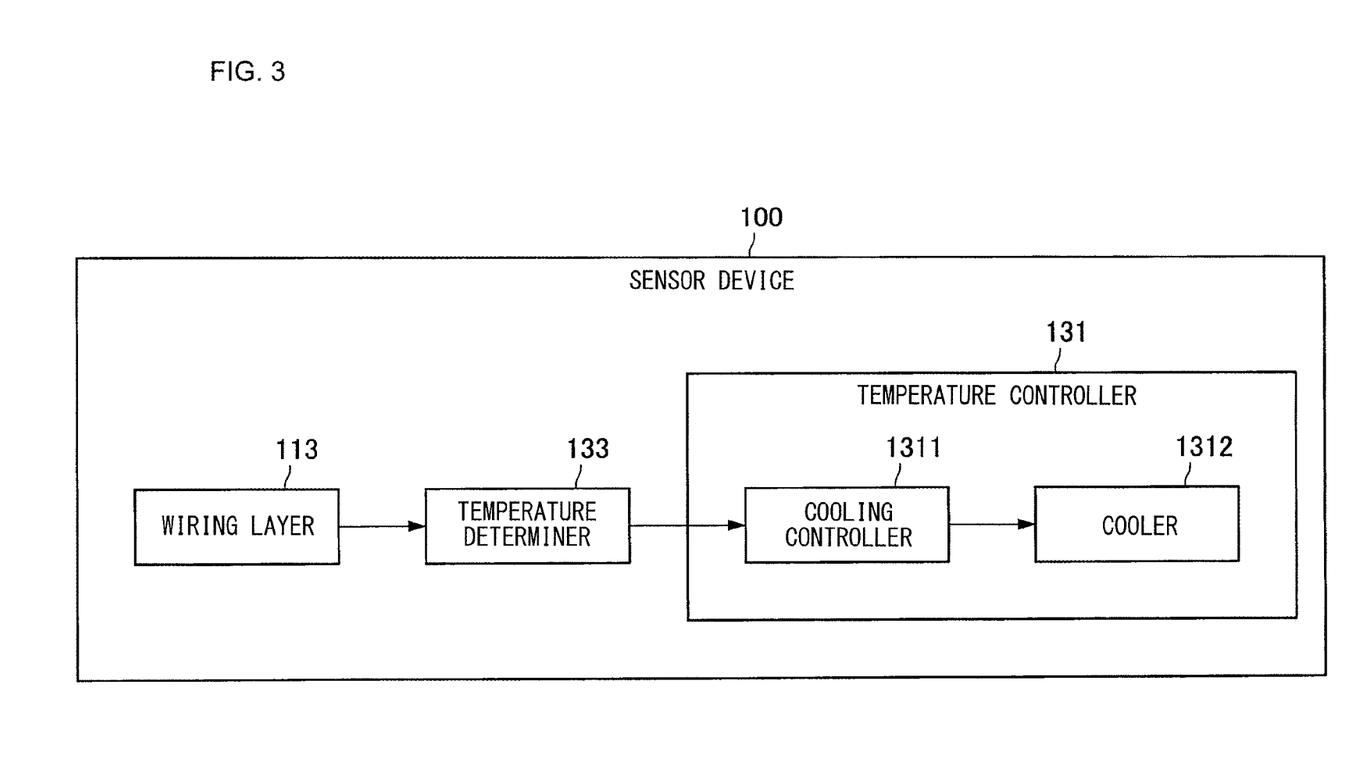
FIG. 3 is a block diagram illustrating a specific control configuration of the sensor device according to the first embodiment.

Subsequently, a specific control configuration of the sensor device 100 according to the present embodiment will be described with reference to FIG. 3. FIG. 3 is a block diagram illustrating the specific control configuration of the sensor device 100 according to the present embodiment.

As illustrated in FIG. 3, the sensor device 100 determines the temperature of the sensing region 140 by using the temperature determiner 133 on the basis of an output from the wiring line layer 113. Thereafter, a cooling controller 1311 in the temperature controller 131 controls driving of a cooler 1312 on the basis of the temperature determined by the temperature determiner 133. Note that the temperature determiner 133 and the cooling controller 1311 may include, for example, hardware such as a MPU (Micro Processing Unit), a CPU (Central Processing Unit), or a microcontroller.

As described above, the wiring line layer 113 includes an electrically conductive material and is provided in the same layer as the electrode array 111 in the semiconductor substrate 110. The electric resistance of the wiring line layer 113 is measured while the wiring line layer 113 is energized constantly or at a predetermined timing.

Figure 4:
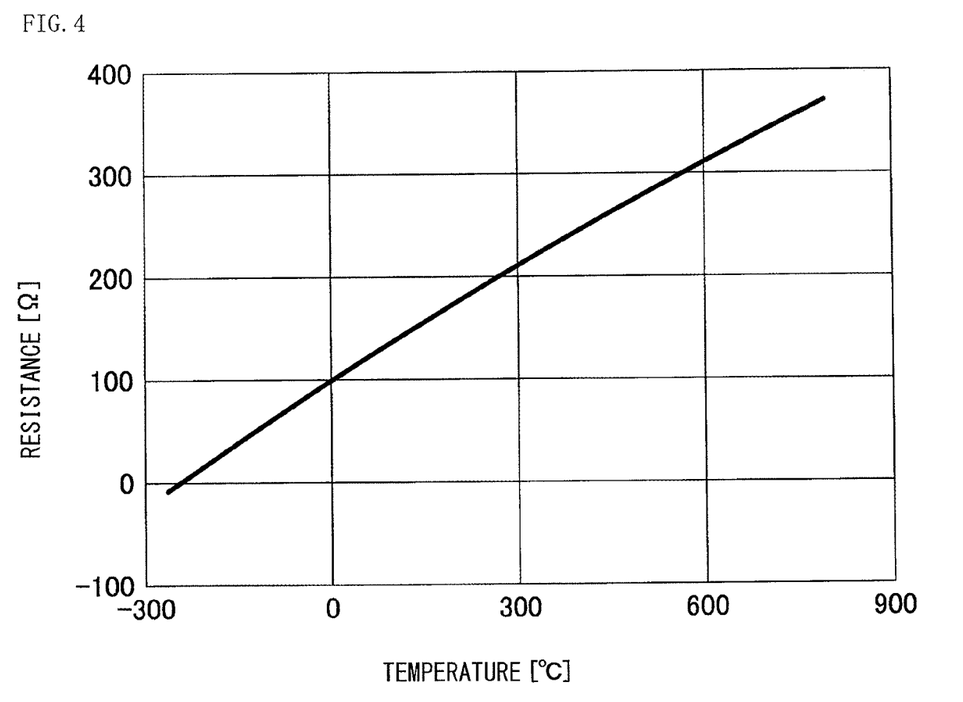
FIG. 4 is a graph illustrating an example of temperature dependency of an electric resistance of a platinum wiring line having a predetermined size.

The temperature determiner 133 determines the temperature of the sensing region 140 on the basis of the electric resistance of the wiring line layer 113. Specifically, first, the temperature determiner 133 determines the electric resistance of the wiring line layer 113 by acquiring a current or a voltage at the time of the energization of the wiring line layer 113. Next, the temperature determiner 133 determines the temperature of the wiring line layer 113 on the basis of the electric resistance of the wiring line layer 113. For example, FIG. 4 illustrates a graph illustrating an example of temperature dependency of the electric resistance of a platinum wiring line. An electric resistance of a conductor such as platinum fluctuates depending on temperature as illustrated in FIG. 4. Therefore, it is possible for the temperature determiner 133 to determine the temperature of the wiring line layer 113 from the electric resistance of the wiring line layer 113 by referring to a graph and the like indicating a relationship between temperature and the electric resistance of the wiring line layer 113 that are measured in advance. Thereafter, the temperature determiner 133 determines the temperature of the sensing region 140 by assuming that the temperature of the sensing region 140 close to or exposed to the wiring line layer 113 be substantially the same as the temperature of the wiring line layer 113.

The cooling controller 1311 controls driving of the cooler 1312 on the basis of the temperature of the sensing region 140 determined by the temperature determiner 133. Specifically, the cooling controller 1311 controls the driving of the cooler 1312 to allow the temperature of the sensing region 140 to fall within a predetermined temperature range. The temperature of the sensing region 140 during the measurement tends to increase due to heat generated from the electrode array 111 in the semiconductor substrate 110, the wiring line layer 113, and the signal processing circuit that executes signal processing on the change in the potential detected by the electrode array 111. Therefore, the cooling controller 1311 may control the cooler 1312 to allow the temperature of the sensing region 140 to fall within the predetermined temperature range by increasing a driving amount of the cooler 1312 in accordance with the increase in the temperature of the sensing region 140.

The cooler 1312 is a cooling mechanism that cools the sensor device 100 (that is, the sensing region 140) on the basis of the control of the cooling controller 1311. For example, the cooler 1312 may be a Peltier element that cools the structural member 125, an air-cooling fan that blows air to the structural member 125, or the like. Note that, the cooler 1312 may be any cooling mechanism which is able to cool the sensor device 100 on the basis of the control of the cooling controller 1311. For example, the cooler 1312 may be a coolant circulator, a compressor, or the like.

(1.3. Variation of Planar Arrangement of Wiring Line Layer)

Next, variation of planar arrangement of the wiring line layer 113 of the sensor device 100 according to the present embodiment will be described with reference to FIGS. 5A to 5D. FIGS. 5A to 5D are top views schematically illustrating examples of the planar arrangement of the wiring line layer 113.

Figure 5A:
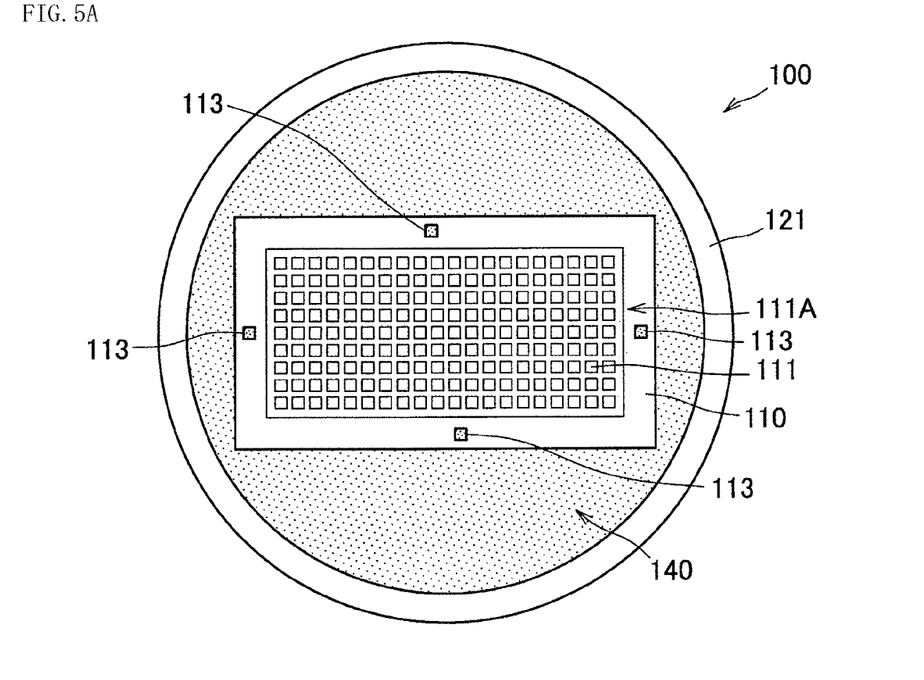
FIG. 5A is a top view schematically illustrating an example of planar arrangement of a wiring line layer.
Figure 5B:
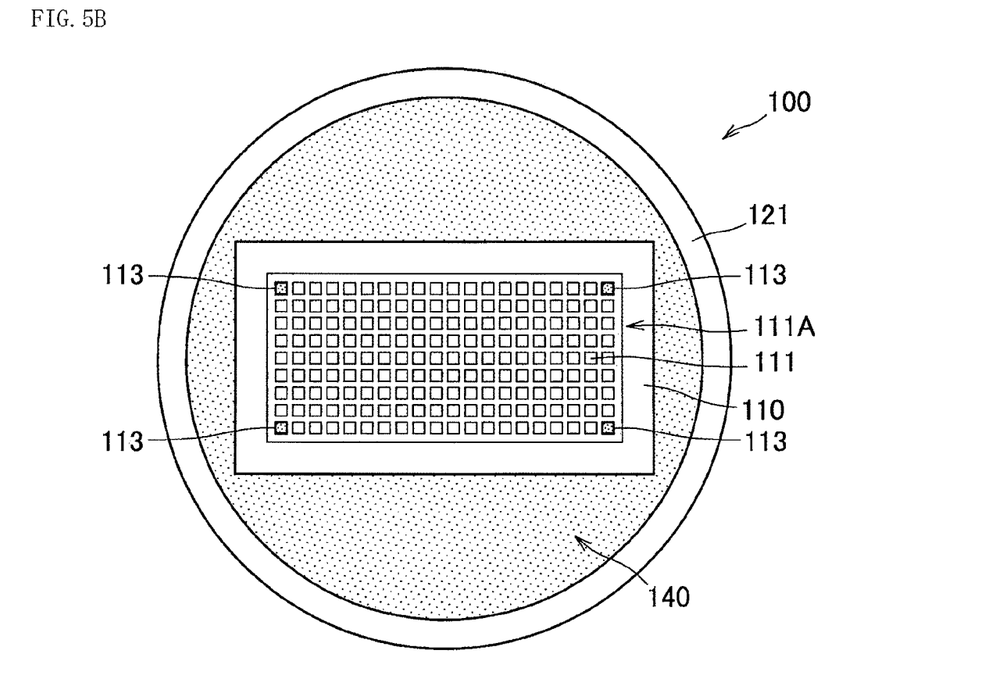
FIG. 5B is a top view schematically illustrating another example of the planar arrangement of the wiring line layer.

As illustrated in FIGS. 5A and 5B, the plurality of wiring line layers 113 may be provided away from each other. Specifically, the wiring line layers 113 may be provided in an upper portion, a lower portion, a left portion, and a right portion inside and outside the array region 111A. There is a possibility that the temperature of the sensing region 140 is not uniform on the same plane depending on a position of a heat source such as the signal processing circuit in the semiconductor substrate 110. Thus, the plurality of wiring line layers 113 is provided away from each other, and the electric resistance of each of the wiring line layers 113 is measured. This enables the sensor device 100 to control the temperature of the sensing region 140 with high in-plane uniformity. In such a case, the electric resistance and the temperature of each of the plurality of wiring line layers 113 provided away from each other may be measured to enable the sensor device 100 to control the temperature of the sensing region 140 for each region where each of the plurality of wiring line layers 113 exists. Alternatively, the sensor device 100 may uniformly control the temperature of the entire sensing region 140 by calculating average values of the electric resistances and the temperatures of the plurality of wiring line layers 113 provided away from each other.

Note that, as illustrated in FIGS. 5A and 5B, the wiring line layer 113 may be provided in the array region 111A where the electrode array 111 is provided or may be provided outside the array region 111A. In order to more accurately determine the temperature of the array region 111A where the measurement target is placed, it is preferable that the wiring line layer 113 be provided in the array region 111A. However, in a case where the wiring line layer 113 is provided in the array region 111A, the area of the array region 111A is reduced in which the detection electrode that detects the change in the potential of the measurement target is to be provided. Therefore, in order to increase the number and the area of the detection electrodes in the electrode array 111, it is preferable that the wiring line layer 113 be provided outside the array region 111A.

Figure 5C:
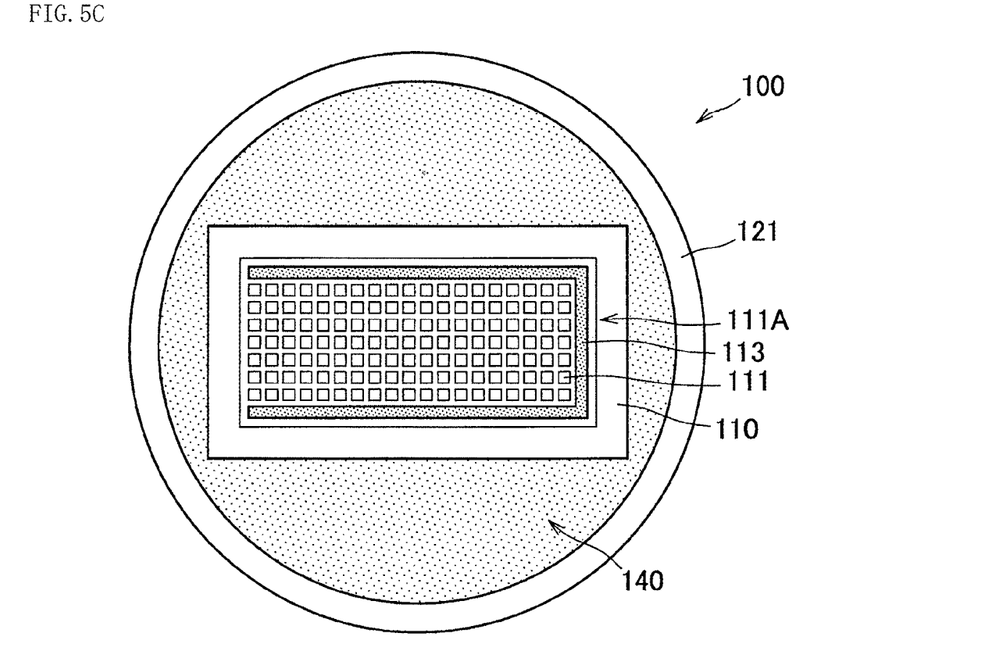
FIG. 5C is a top view schematically illustrating still another example of the planar arrangement of the wiring line layer.

As illustrated in FIG. 5C, the wiring line layer 113 may be provided in a linear shape surrounding the periphery of the array region 111A where the electrode array 111 is provided. Specifically, the wiring line layer 113 may be provided in a linear shape that extends as curving in three directions along the periphery of the array region 111A. As described above, there is a possibility that the temperature of the sensing region 140 is not uniform on the same plane. Therefore, by providing the wiring line layer 113 having a linear shape in a wide range, it is possible to reflect the temperature of the sensing region 140 in a wider range on the electric resistance of the wiring line layer 113. This allows the temperature of the sensing region 140 to be determined with higher accuracy, and it therefore is possible for the sensor device 100 to control the temperature of the sensing region 140 with higher accuracy by using the temperature controller 131.

Figure 5D:
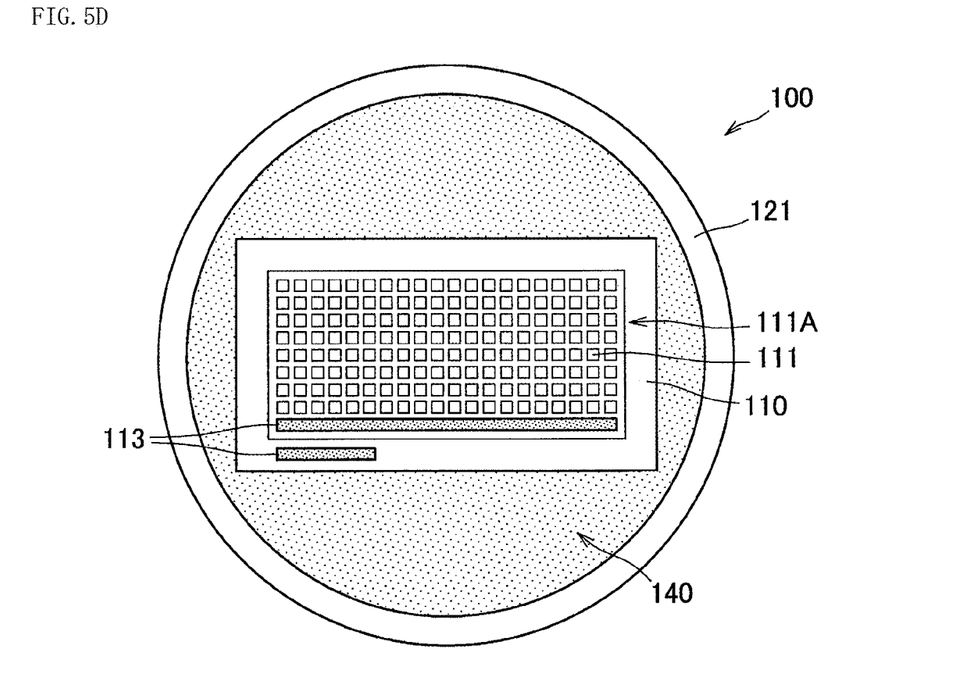
FIG. 5D is a top view schematically illustrating yet another example of the planar arrangement of the wiring line layer.

As illustrated in FIG. 5D, a plurality of wiring line layers 113 may be provided, and the wiring line layers 113 may have at least two or more different planar shapes. Specifically, a plurality of linear-shaped wiring line layers 113 that extends by different lengths may be provided. In such a case, it is possible for the temperature determiner 133 to measure the electric resistance of the wiring line layer 113 with higher accuracy by obtaining a ratio of the electric resistances of the respective wiring line layers 113. This enables the sensor device 100 to determine the temperature of the sensing region 140 with higher accuracy, and it therefore is possible for the temperature controller 131 to control the temperature of the sensing region 140 with high accuracy. Note that, at this time, the plurality of wiring line layers 113 may be provided at places close to each other in the sensing region 140 in order to measure the temperature of the same region.

Note that it is possible to combine the variations of the planar arrangement of the wiring line layer 113 illustrated in FIGS. 5A to 5D. For example, the plurality of wiring line layers 113 may be provided around the array region 111A and the wiring line layers 113 may have at least two or more different planar shapes.

(1.4. Modification Example of Sensor Device)

Figure 6:
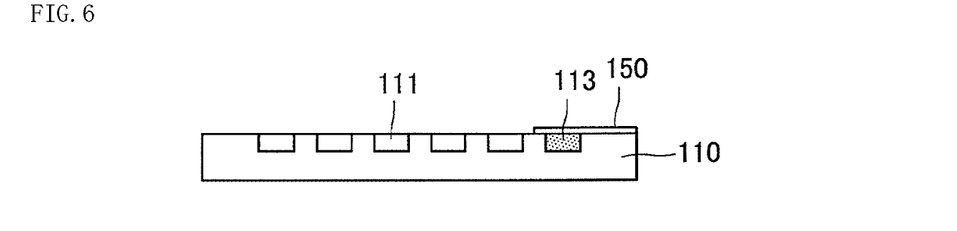
FIG. 6 is a cross-sectional diagram schematically illustrating a configuration of a semiconductor substrate of a sensor device according to a modification example of the first embodiment.

Moreover, a modification example of the sensor device 100 according to the present embodiment will be described with reference to FIG. 6. FIG. 6 is a cross-sectional diagram schematically illustrating a configuration of the semiconductor substrate 110 of the sensor device 100 according to the modification example.

As illustrated in FIG. 6, in the sensor device 100 according to the modification example, a protection film 150 may be provided on the wiring line layer 113.

The protection film 150 isolates the wiring line layer 113 from the sensing region 140 and protects the wiring line layer 113 from being exposed to the sensing region 140. It is possible to form the protection film 150 by using any material that has water resistance or waterproof property. For example, the protection film 150 may include an inorganic insulating material such as silicon oxide or silicon nitride, various resins, or various rubbers.

Since it is sufficient that the temperature of the wiring line layer 113 be substantially the same as the temperature of the sensing region 140, it is sufficient that the wiring line layer 113 be close to the sensing region 140. That is, it is not necessary for the wiring line layer 113 to be exposed to the sensing region 140, and the wiring line layer 113 may be isolated from the sensing region 140 by the protection film 150. In such a case, since the wiring line layer 113 is not exposed to the sensing region 140, it is possible to prevent the elution of the material of the wiring line layer 113 into the solution 141. Therefore, it is possible for the sensor device 100 according to the modification example to form the wiring line layer 113 by using metal or the like that may affect the measurement target such as a living cell. Therefore, it is possible for the sensor device 100 according to the modification example to improve a degree of freedom in selection of the material of the wiring line layer 113.

(1.5. Summary of Sensor Device)

According to the sensor device 100 of the present embodiment described above, it is possible to determine the temperature of the sensing region 140 on the basis of the electric resistance of the wiring line layer 113 provided in the same layer as the electrode array 111. This enables the sensor device 100 to determine the temperature of the sensing region 140 with a simple structure, and it therefore is possible to more appropriately control the temperature of the sensing region 140.

For example, in a case where the calorific value from the semiconductor substrate 110 is large (for example, in a case where a large number of detection electrodes are integrated on the electrode array 111 or in a case where various signal processing is executed on the semiconductor substrate 110), it is possible for the sensor device 100 according to the present embodiment to more preferably control the temperature of the sensing region 140. Furthermore, for example, in a case where the action potential of the living cell that needs strict temperature control is measured in the sensing region 140, it is possible to more preferably use the sensor device 100 according to the present embodiment.

<2. Measurement Apparatus>

Figure 7:
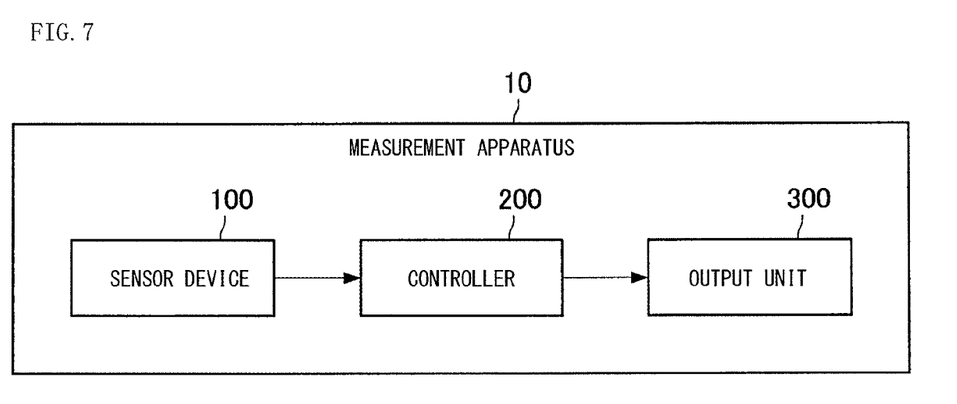
FIG. 7 is a block diagram illustrating a configuration of a measurement apparatus according to a second embodiment of the present disclosure.

Next, a configuration of a measurement apparatus according to a second embodiment of the present disclosure will be described with reference to FIG. 7. FIG. 7 is a block diagram illustrating the configuration of the measurement apparatus according to the present embodiment.

As illustrated in FIG. 7, a measurement apparatus 10 according to the present embodiment is a measurement apparatus that includes the sensor device 100 according to the first embodiment. The measurement apparatus 10 includes, for example, the sensor device 100 according to the first embodiment, a controller 200 that controls an operation of the entire measurement apparatus 10, and an output unit 300 that outputs a result measured by the sensor device 100 to the outside.

As described above, the sensor device 100 is a potential measurement device that detects a change in a potential of a measurement target. Since it is possible for the sensor device 100 to determine a temperature of the sensing region 140 with a simple structure, it is possible to measure the change in the potential of the measurement target while appropriately controlling the temperature of the sensing region 140. For example, the sensor device 100 may be a potential measurement device that measures an action potential of a living cell such as a cardiomyocyte or a nerve cell while controlling the temperature of the sensing region 140 at a constant level.

The controller 200 includes, for example, hardware such as a CPU (Central Processing Unit), a ROM (Read Only Memory), a RAM (Random Access Memory), or the like and controls the operation of the entire measurement apparatus 10. Specifically, the CPU functions as an arithmetic processing unit and controls an overall operation of the measurement apparatus 10 according to a program stored in the ROM or the like. The ROM stores a program and an arithmetic parameter to be used by the CPU, and the RAM temporarily stores the program to be used in the execution by the CPU, a parameter that appropriately varies during the execution, and the like. For example, the controller 200 may receive a measurement result from the sensor device 100 and convert the received measurement result into a form or a format that is outputtable to the outside.

The output unit 300 receives the measurement result of the sensor device 100 from the controller 200 and outputs the received measurement result to the outside. For example, the output unit 300 may be a printer that prints the measurement result of the sensor device 100 on a sheet or a display device that displays the measurement result of the sensor device 100 on a display. Alternatively, the output unit 300 may be a connection interface or a communication device that outputs the measurement result of the sensor device 100 to an external device. For example, the output unit 300 may be a connection interface such as a USB port or an optical audio terminal or may be a wired or wireless LAN compliant communication device or a cable communication device.

Preferred embodiments of the present disclosure have been described above in detail with reference to the attached drawings. However, the technical scope of the present disclosure is not limited to the above examples. It is obvious that a person who has normal knowledge in the technical field of the present disclosure may arrive at various changed examples and modified examples within the technical idea described in claims, and it is understood that these examples naturally belong to the technical scope of the present disclosure.

Furthermore, the effects described herein are only explanatory and exemplary and are not limited. In other words, the technology according to the present disclosure may apply another effect that is obvious to a person skilled in the art from the description herein together with the above effects or instead of the above effects.

Note that the following configurations also fall within the technical scope of the present disclosure.

(1)

A sensor device including:

an electrode array exposed to a sensing region;

at least one or more wiring line layers provided in a layer same as the electrode array;

a temperature determiner that determines a temperature of the sensing region on a basis of an electric resistance of the wiring line layer; and a temperature controller that controls the temperature of the sensing region on a basis of the temperature of the sensing region determined by the temperature determiner.

(2)

The sensor device according to (1), in which the temperature controller controls the temperature of the sensing region to allow the temperature of the sensing region to fall within a predetermined temperature range.

(3)

The sensor device according to (1) or (2), in which the temperature controller includes a cooling mechanism.

(4)

The sensor device according to any one of (1) to (3), in which the electrode array and the wiring line layer are provided on one main surface of a semiconductor substrate.

(5)

The sensor device according to (4), in which the semiconductor substrate is provided with a signal processing circuit that executes signal processing on a signal from the electrode array.

(6)

The sensor device according to (4) or (5), in which the sensing region is an inner region of a recess structure surrounded by a bottom portion including the semiconductor substrate and a sidewall provided around the bottom portion.

(7)

The sensor device according to any one of (1) to (6), in which the wiring line layer is provided on an inner side of an array region where the electrode array is provided.

(8)

The sensor device according to any one of (1) to (7), in which a plurality of the wiring line layers having a planar shape is provided away from each other.

(9)

The sensor device according to (8), in which
the plurality of the wiring line layers is provided, and
the wiring line layers have at least two or more different planar shapes.

(10)

The sensor device according to any one of (1) to (9), in which
the wiring line layer is isolated from the sensing region by a protection film.

(11)

The sensor device according to any one of (1) to (10), in which
the wiring line layer and the electrode array include same material.

(12)

The sensor device according to any one of (1) to (11), in which
the wiring line layer includes noble metal.

(13)

The sensor device according to any one of (1) to (12), in which
the electrode array includes a plurality of detection electrodes that detects a potential at each position of the sensing region and a reference electrode that detects a reference potential.

(14)

A measurement apparatus including:
a sensor device; and
an information processing device that executes information processing on an output from the sensor device, in which
the sensor device includes
an electrode array exposed to a sensing region,
at least one or more wiring line layers provided in a layer same as the electrode array,
a temperature determiner that determines a temperature of the sensing region on a basis of an electric resistance of the wiring line layer, and
a temperature controller that controls the temperature of the sensing region on a basis of the temperature of the sensing region determined by the temperature determiner.

REFERENCE SIGNS LIST

10: Measurement apparatus
100: Sensor device
110: Semiconductor substrate
111: Electrode array
111A: Array region
113: Wiring line layer
121: Sidewall
125: Structural member
131: Temperature controller
133: Temperature determiner
140: Sensing region
141: Solution
150: Protection film
200: Controller
300: Output unit

The invention claimed is:

1. A sensor device, comprising:
a substrate;
an electrode matrix array of electrodes provided in a layer of a surface of the substrate and exposed to a sensing region;
at least one wiring line layer provided in the layer of the surface of the substrate substantially arrayed with the electrode matrix array,
wherein there are fewer wiring line layers than electrodes of the electrode matrix array, and
wherein each wiring line layer is electrically isolated from all of the electrodes in the electrode matrix array;
a temperature determiner that determines a temperature of the sensing region on a basis of an electric resistance of the at least one wiring line layer; and
a temperature controller that controls the temperature of the sensing region on a basis of the temperature of the sensing region determined by the temperature determiner.

2. The sensor device according to claim 1, wherein the temperature controller controls the temperature of the sensing region to allow the temperature of the sensing region to fall within a predetermined temperature range.

3. The sensor device according to claim 1, wherein the temperature controller includes a cooling mechanism.

4. The sensor device according to claim 1, wherein the substrate is a semiconductor substrate and electrode matrix array and the at least one wiring line layer are provided on a main surface of the semiconductor substrate.

5. The sensor device according to claim 4, wherein the semiconductor substrate is provided with a signal processing circuit that executes signal processing on a signal from the electrode matrix array.

6. The sensor device according to claim 4, wherein the sensing region is an inner region of a recess structure surrounded by a bottom portion including the semiconductor substrate and a sidewall provided around the bottom portion.

7. The sensor device according to claim 1, wherein the at least one wiring line layer is provided on an inner side of an array region where the electrode matrix array is provided.

8. The sensor device according to claim 1, wherein the at least one wiring line layer includes a plurality of the wiring line layers having a planar shape and separated from each other.

9. The sensor device according to claim 1, wherein each wiring line layer is in direct electrical communication with the temperature determiner.

10. The sensor device according to claim 1, wherein the at least one wiring line layer is isolated from the sensing region by a protection film.

11. The sensor device according to claim 1, wherein the at least one wiring line layer and the electrode matrix array include the same material.

12. The sensor device according to claim 1, wherein the at least one wiring line layer includes a noble metal.

13. The sensor device according to claim 1, wherein the electrode matrix array includes a plurality of detection electrodes that detects a potential at each position of the sensing region and a reference electrode that detects a reference potential.

14. A measurement apparatus, comprising:
a sensor device; and
an information processing device that executes information processing on an output from the sensor device,
wherein the sensor device includes:
a substrate;
an electrode matrix array of electrodes provided in a layer of a surface of the substrate and exposed to a sensing region;
at least one wiring line layer provided in the layer of the surface of the substrate substantially arrayed with the electrode matrix array, wherein there are fewer wiring line layers than electrodes of the electrode matrix array, and wherein each wiring line layer is electrically isolated from all of the electrodes in the electrode matrix array;

a temperature determiner that determines a temperature of the sensing region on a basis of an electric resistance of the at least one wiring line layer; and a temperature controller that controls the temperature of the sensing region on a basis of the temperature of the sensing region determined by the temperature determiner.

15. The measurement apparatus according to claim 14, wherein the at least one wiring line layer includes a plurality of the wiring line layers having a planar shape and separated from each other.

16. The measurement apparatus according to claim 14, wherein the at least one wiring line layer is isolated from the sensing region by a protection film.

17. The measurement apparatus according to claim 14, wherein the at least one wiring line layer and the electrode matrix array include the same material.

18. The measurement apparatus according to claim 14, wherein the at least one wiring line layer includes a noble metal.

19. The measurement apparatus according to claim 14, wherein the electrode matrix array includes a plurality of detection electrodes that detects a potential at each position of the sensing region and a reference electrode that detects a reference potential.

20. The measurement apparatus according to claim 14, wherein each wiring line layer is in direct electrical communication with the temperature determiner.

* * * * *